United States Patent
Keys et al.

(10) Patent No.: US 7,195,875 B2
(45) Date of Patent: Mar. 27, 2007

(54) OLIGONUCLEOTIDE PAIRS FOR MULTIPLEXED BINDING ASSAYS

(75) Inventors: Daniel A. Keys, Irvine, CA (US); Parameswara Meda Reddy, Brea, CA (US); Jackie S. Bodnar, Fullerton, CA (US); Firdous Farooqui, Brea, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 515 days.

(21) Appl. No.: 10/419,020

(22) Filed: Apr. 18, 2003

(65) Prior Publication Data

US 2004/0209261 A1 Oct. 21, 2004

(51) Int. Cl.
*C12Q 1/68* (2006.01)
*C07H 21/04* (2006.01)

(52) U.S. Cl. .......................................... 435/6; 536/23.1

(58) Field of Classification Search ..................... None
See application file for complete search history.

(56) References Cited

U.S. PATENT DOCUMENTS

| | | | |
|---|---|---|---|
| 5,604,097 A | 2/1997 | Brenner ......................... | 435/6 |
| 5,635,400 A | 6/1997 | Brenner ................... | 435/320.1 |
| 5,654,413 A | 8/1997 | Brenner ..................... | 536/22.1 |
| 5,807,683 A | 9/1998 | Brenner ...................... | 435/7.1 |
| 5,846,719 A | 12/1998 | Brenner et al. ................ | 435/6 |
| 5,863,722 A | 1/1999 | Brenner ......................... | 435/6 |
| 6,140,489 A | 10/2000 | Brenner ..................... | 536/24.3 |
| 6,146,833 A | 11/2000 | Milton ........................... | 435/6 |
| 6,172,214 B1 | 1/2001 | Brenner ..................... | 536/24.3 |
| 6,172,218 B1 | 1/2001 | Brënner ..................... | 536/25.4 |
| 6,235,475 B1 | 5/2001 | Brenner et al. ................ | 435/6 |
| 6,352,828 B1 | 3/2002 | Brenner ......................... | 435/6 |
| 2005/0026164 A1* | 2/2005 | Zhou ........................... | 435/6 |

FOREIGN PATENT DOCUMENTS

WO WO 96/06948 3/1996
WO WO 02/16649 2/2002

OTHER PUBLICATIONS

Agrawal, Sudhir et al., *Site Specific Functionalization of Oligonucleotidesfor Attaching Two Different Reporter Groups*, Nucleic Acids Research, 18:5419-5423 (1990).
Matson, Robert et al., *Biopolymer Synthesis on Polypropylene Supports: Oligonucleotide Arrays*, Analytical; Biochemistry 224, 110-116 (1995).
Ozaki, Hiroaki et al., *The Estimation of Distances Between Specific Backbone-Labeled Sites in DNA Using Fluorescence Resonance Energy Transfer*, Nucleic Acids Research, 20:5205-5214 (1992).
Uhlmann, Eugen, *Antisense Oligonucleotides: A New Therapeutic Principle*, Chemical Reviews, 90:543-584 (1990).
Oligonucleotide Properties Calculator, http://www.basic.nwu.edu/biotools/oligocalc.html.
Ben-Dor, A. et al., "Universal DNA Tag Systems: A Combinatorial Design Scheme," *Journal of Computational Biology*,7(3/4):503-519 (2000).
Gerry, Norman P. et al., Universal DNA Microarray method for Multiplex Detection of Low Abundance Point Mutations, *Journal of Molecular Biology*, 292(2):251-262 (Sep. 17, 1999).
Shoemaker, D.D. et al., "Quantitative phenotypic analysis of yeast deletion mutants using a highly parallel molecular bar-coding strategy," *Nature Genetics*, 14(4):451,452,455 (Dec. 1, 1996).

\* cited by examiner

*Primary Examiner*—James Martinell
(74) *Attorney, Agent, or Firm*—Sheldon Mak Rose & Anderson PC

(57) ABSTRACT

The invention is an oligonucleotide-based assay system and kit useful for sorting, detecting, and identifying analytes. The system utilizes complementary oligonucleotide pairs in which one oligonucleotide of each pair is immobilized to a solid substrate and the other oligonucleotide has an analyte binding agent attached to it. The different oligonucleotide pairs hybridize at substantially the same rate, have substantially the same Tm, have nucleotide sequences designed to minimize cross-hybridization between different pairs, and hybridize together relatively rapidly at ambient temperatures without detectable cross-hybridization.

24 Claims, 1 Drawing Sheet

SEQUENCE LISTING

```
<160> NUMBER OF SEQ ID NOS: 188

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atactgactg gcgatgctgt cgaagtagcg                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgctacttcg acagcatcgc cagtcagtat                                    30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agttaaatag cttgcaaaat acgtggcctt                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaggccacgt attttgcaag ctatttaact                                    30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gaagccatac caaacgacga gcgtgacacc                                    30
```

```
<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtgtcacgc tcgtcgtttg gtatggcttc                                          30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcttaccgaa tacggcttgg agaacctatc                                          30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gataggttct ccaagccgta ttcggtaagc                                          30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcgtggtccg cgatcttcct acgattgatg                                          30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
catcaatcgt aggaagatcg cggaccacgc                                          30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttgaggttt cggagcgttc cgtgcatcgc                                          30
```

```
<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcgatgcacg gaacgctccg aaacctcaaa                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aatcctgttg tgagccgacc aagtgcctcc                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggaggcactt ggtcggctca caacaggatt                                    30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtatctgacg cgtatgccca ggttagtggc                                    30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gccactaacc tgggcatacg cgtcagatac                                    30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cggagtcgtc ctctgtaggg atttgcccTt                                    30
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
aagggcaaat ccctacagag gacgactccg                              30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
caggctgtgg agtgctattg tcatatgggc                              30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
gcccatatga caatagcact ccacagcctg                              30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
tcttctctct ggtctaaggc atcgagcgga                              30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
tccgctcgat gccttagacc agagagaaga                              30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
tggcgtacta gtgcttaggc gtactgaagc                              30

<210> SEQ ID NO 24

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcttcagtac gcctaagcac tagtacgcca                                    30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgctggcttt actgcgacgg tgactctcct                                    30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aggagagtca ccgtcgcagt aaagccagca                                    30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctatcaaagc tggttccagg cgctcctgga                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tccaggagcg cctggaacca gctttgatag                                    30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgaggcaagt acattagttc tcagccggcg                                    30

<210> SEQ ID NO 30
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cgccggctga gaactaatgt acttgcctca                                          30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcttgggtta gattgtgttt gccgagccaa                                          30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttggctcggc aaacacaatc taacccaagc                                          30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgtccattcc tatcgggagg taacagactt                                          30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aagtctgtta cctcccgata ggaatggacg                                          30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ctaaggagtc cgaagatgta caatgggtcg                                          30

<210> SEQ ID NO 36
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 36
cgacccattg tacatcttcg gactccttag                                30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aactagccgc ctcctgtccc atgaattcta                                30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tagaattcat gggacaggag gcggctagtt                                30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agcttcttgt aacgttgagt tgcaggtccg                                30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cggacctgca actcaacgtt acaagaagct                                30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cactggataa ttgcgccttc cgtgcatgaa                                30

<210> SEQ ID NO 42
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 42
ttcatgcacg gaaggcgcaa ttatccagtg                                      30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cccgcgcaga gcgtagttgt aatttagatc                                      30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gatctaaatt acaactacgc tctgcgcggg                                      30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cctggaaata agcagcagca ccaactctca                                      30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgagagttgg tgctgctgct tatttccagg                                      30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggctcatggt tctttgctca accataagcc                                      30

<210> SEQ ID NO 48
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 48
ggcttatggt tgagcaaaga accatgagcc                                          30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cttgctcctc acatgatgcg gaaacgctaa                                          30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttagcgtttc cgcatcatgt gaggagcaag                                          30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atccttctgc actttcgcgt agacatagcc                                          30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggctatgtct acgcgaaagt gcagaaggat                                          30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atcgaaccca aactgaggtt aagagccgct                                          30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
agcggctctt aacctcagtt tgggttcgat                                30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aaggactgga cgttgcattc acagtgggtt                                30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aacccactgt gaatgcaacg tccagtcctt                                30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ctcatgaagg ccgtcgggaa attccaagtt                                30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aacttggaat ttcccgacgg ccttcatgag                                30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tggattccgt tatcaccatt tggaccctgc                                30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
-continued

<400> SEQUENCE: 60
gcagggtcca aatggtgata acggaatcca                                              30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
taagggctct atctaccacc tccgactttc                                              30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gaaagtcgga ggtggtagat agagccctta                                              30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tacgctccca gtgtgatcac caaagcttac                                              30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gtaagctttg gtgatcacac tgggagcgta                                              30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agactgaact accggcggtt gcactactaa                                              30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 66
ttagtagtgc aaccgccggt agttcagtct                                30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gccaaacacg cccaatcact gttacatgtc                                30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gacatgtaac agtgattggg cgtgtttggc                                30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gcttgacgtc taccaccgtg aacataagga                                30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tccttatgtt cacggtggta gacgtcaagc                                30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aagaaccgta ataggcccgg ttgggaattc                                30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
```
gaattcccaa ccgggcctat tacggttctt                     30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cggactaaca agactcttat agcgtctcgc                     30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gcgagacgct ataagagtct tgttagtccg                     30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tcgccaacgt agctgtgcta cagttgattc                     30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gaatcaactg tagcacagct acgttggcga                     30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gcagcggcta aaccttgaga tcgaatggaa                     30

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ttccattcga tctcaaggtt tagccgctgc                                30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcaaccgtca acggtcttaa tgacacatcg                                30

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cgatgtgtca ttaagaccgt tgacggttgc                                30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gggtagaaac ggacgttacc catgatcttg                                30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
caagatcatg ggtaacgtcc gtttctaccc                                30

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggcggcaaca cctaccttct agattgaaac                                30

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gtttcaatct agaaggtagg tgttgccgcc                                30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
cgctaatagt ggaccctctc atagctatgg                                    30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
ccatagctat gagagggtcc actattagcg                                    30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
ctgatggaat ctaccactgc taaacgcagc                                    30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
gctgcgttta gcagtggtag attccatcag                                    30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
gcctagtcgg atgctcggat atcatactac                                    30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
gtagtatgat atccgagcat ccgactaggc                                    30

```
<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ctttgaacga catcttagtc tcgaacgccg                                    30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cggcgttcga gactaagatg tcgttcaaag                                    30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tcgacatgcg cgtcatctga tactgcggtc                                    30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gaccgcagta tcagatgacg cgcatgtcga                                    30

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggtggcctcg taaggcgaga attagggttg                                    30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
caaccctaat tctcgcctta cgaggccacc                                    30
```

```
<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggctagatag gcgattagtc agagtggaca                                            30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tgtccactct gactaatcgc ctatctagcc                                            30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cctggataag acgttaacgt tacggagcca                                            30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tggctccgta acgttaacgt cttatccagg                                            30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
caaactgagc taggcctaac tgtgatgcag                                            30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ctgcatcaca gttaggccta gctcagtttg                                            30

<210> SEQ ID NO 103
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cgcctcgtgt gttataacga tgggactttg                                    30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
caaagtccca tcgttataac acacgaggcg                                    30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tggtttagcc tttccggcat ctgctgtaca                                    30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tgtacagcag atgccggaaa ggctaaacca                                    30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
caacctctac ccagaaactc aagtttcggc                                    30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gccgaaactt gagtttctgg gtagaggttg                                    30

<210> SEQ ID NO 109
<211> LENGTH: 30
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ctcgtttcta ggtcactgcg caaaacgctt                                     30

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aagcgttttg cgcagtgacc tagaaacgag                                     30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tgctcttctc gtgcccgtta aaggatcgat                                     30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atcgatcctt taacgggcac gagaagagca                                     30

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
cccggcaggt atacaaagca cttcgtatac                                     30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gtatacgaag tgctttgtat acctgccggg                                     30

<210> SEQ ID NO 115
<211> LENGTH: 30
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 115
gtagaagcct gtggttaaaa ctatggcccg                                30

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cgggccatag ttttaaccac aggcttctac                                30

<210> SEQ ID NO 117
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
catcggtcga acccgtgtca acaagattct                                30

<210> SEQ ID NO 118
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
agaatcttgt tgacacgggt tcgaccgatg                                30

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tggaggagac ttgtcaggat ttgctctgag                                30

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ctcagagcaa atcctgacaa gtctcctcca                                30

<210> SEQ ID NO 121
<211> LENGTH: 30
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 121
agcccaagga atagtcaata cttcctcagc                                          30

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gctgaggaag tattgactat tccttgggct                                          30

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
caaaggaaat gttcgagccg ccagactaga                                          30

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tctagtctgg cggctcgaac atttcctttg                                          30

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tcctattatg cctgaattca ggcagccgac                                          30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gtcggctgcc tgaattcagg cataatagga                                          30

<210> SEQ ID NO 127
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 127
gcatgtgtag atggccagcc acttattagg                                          30

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cctaataagt ggctggccat ctacacatgc                                          30

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cctttgggta ttgctctgac ctggttatgc                                          30

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gcataaccag gtcagagcaa tacccaaagg                                          30

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aggcaggtcc ctagtcacaa cttaatctgc                                          30

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gcagattaag ttgtgactag ggacctgcct                                          30

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic -continued

<400> SEQUENCE: 133
ccgacagtac tttactcatt gtggcgcagt                              30

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
actgcgccac aatgagtaaa gtactgtcgg                              30

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aagtgaaagc atctccgcat gcattggcca                              30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tggccaatgc atgcggagat gctttcactt                              30

<210> SEQ ID NO 137
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gcacgtacac gagaaacggg tatctaagct                              30

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agcttagata cccgtttctc gtgtacgtgc                              30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 139
tccagctgca gacaaagacc tatgcgttac                                          30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gtaacgcata ggtctttgtc tgcagctgga                                          30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
atccgactca tctaggtgca cctctatgtg                                          30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cacatagagg tgcacctaga tgagtcggat                                          30

<210> SEQ ID NO 143
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ctggacgact ttctagatgc cctgagttac                                          30

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gtaactcagg gcatctagaa agtcgtccag                                          30

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 145
ctaagacaca tcctattatc ctgcccgagc      30

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gctcgggcag gataatagga tgtgtcttag      30

<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
agaattgcgc acaagaagtc tctgcggcaa      30

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ttgccgcaga gacttcttgt gcgcaattct      30

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ccgagcacta taggagttat aatcgagggg      30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cccctcgatt ataactccta tagtgctcgg      30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ctagttaccc acacttagtc acttgcagcg                                30

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cgctgcaagt gactaagtgt gggtaactag                                30

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcaaatcagt aaagatggac aggcctaccc                                30

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gggtaggcct gtccatcttt actgatttgc                                30

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
atggtcgcat gatttagtac ggatggcgtg                                30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cacgccatcc gtactaaatc atgcgaccat                                30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aacattcttc tcgggttaca aaccgcgcga                                    30

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tcgcgcggtt tgtaacccga gaagaatgtt                                    30

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ggcaagactc gttctgggct gcttattaga                                    30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tctaataagc agcccagaac gagtcttgcc                                    30

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ccatatcacg tgatgccgga attgtcacgt                                    30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
acgtgacaat tccggcatca cgtgatatgg                                    30

<210> SEQ ID NO 163
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tgcgatatac tccatgcctc tcttggcgga                                    30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tccgccaaga gaggcatgga gtatatcgca                                      30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gtgtgcgcgc cttctagaat actcataagc                                      30

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
gcttatgagt attctagaag gcgcgcacac                                      30

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ccagcacaaa cgctgatcgt tgaaacggat                                      30

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
atccgtttca acgatcagcg tttgtgctgg                                      30

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aagtgtgagg tcgttcactt tcacactgcc                                      30

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
ggcagtgtga aagtgaacga cctcacactt              30

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
taaatcaacg gcattggcgt ccgttatcgc              30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
gcgataacgg acgccaatgc cgttgattta              30

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
tgcgcccaca cgttacgatc tgtataaagc              30

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
gctttataca gatcgtaacg tgtgggcgca              30

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 175
ataatgcgtt tccggccacc gcgttattac              30

<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gtaataacgc ggtggccgga aacgcattat                                      30

<210> SEQ ID NO 177
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tcaacgcgcg gtttcttgag taattcagcc                                      30

<210> SEQ ID NO 178
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ggctgaatta ctcaagaaac cgcgcgttga                                      30

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gcaccggagg tttacatcat gcagaagtgt                                      30

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
acacttctgc atgatgtaaa cctccggtgc                                      30

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tgtctcacta gagcttcacc catgcatgtg                                      30

<210> SEQ ID NO 182

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cacatgcatg ggtgaagctc tagtgagaca                                     30

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gccaaacata gttggaatcc tcgggaggaa                                     30

<210> SEQ ID NO 184
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ttcctcccga ggattccaac tatgtttggc                                     30

<210> SEQ ID NO 185
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gcactataaa cttcctagcc ttctcgtcgc                                     30

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gcgacgagaa ggctaggaag tttatagtgc                                     30

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ggtttgcaag aagcagaagc cattccgaca                                     30

<210> SEQ ID NO 188
<211> LENGTH: 30
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
tgtcggaatg gcttctgctt cttgcaaacc                              30
```

OLIGONUCLEOTIDE PAIRS FOR MULTIPLEXED BINDING ASSAYS

BACKGROUND

Figure 1:
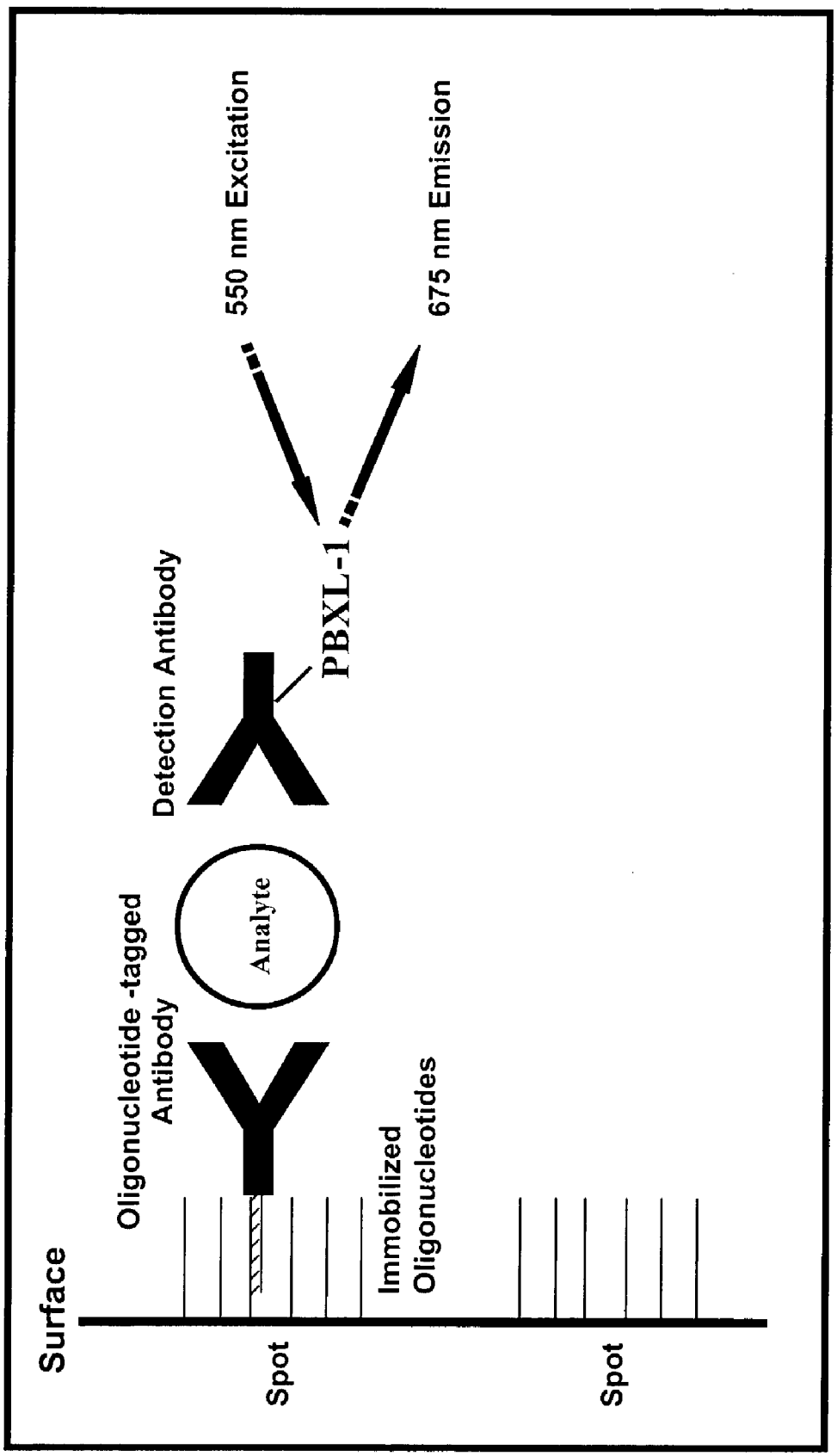

The following description provides a summary of information relevant to the present invention and is not an indication that any of the information provided or publications referenced herein is prior art to the presently claimed invention.

The hybridization of oligonucleotides is useful for a wide variety of analytical and diagnostic assays, including the sorting, detection, and identification of analytes. It is important that the non-complementary oligonucleotides do not cross-hybridize with one another in such assays. Cross-hybridization of oligonucleotides is in part due to the variability in base-stacking energies among the different nucleotides and nucleotide sequence variations within oligonucleotides. Another set of parameters effecting oligonucleotide cross-hybridization is the hybridization reaction conditions. Unfortunately, such non-specific cross-hybridization is a common problem and is the primary cause of false positive or false negative signals in oligonucleotide-based assays, in particular where multiple oligonucleotide pairs are employed.

Other factors that pose problems to the design and implementation of an assay system utilizing multiple oligonucleotides are the desirability that substantially all of the paired oligonucleotides have substantially the same Tm, that all paired oligonucleotides hybridize at substantially the same rate and within the same time frame, and the desirability that the oligonucleotides hybridize together relatively rapidly at ambient temperatures without significant cross-hybridization.

What is needed is an oligonucleotide-based assay system useful for the detection of multiple analytes that utilizes a set of oligonucleotide pairs having no significant cross-hybridization between different pairs, and no consequent false positive or negative signals. A need also exists for an oligonucleotide-based assay system where all paired oligonucleotides hybridize at substantially the same rate, have substantially the same Tm, and where complementary oligonucleotide pairs are able to hybridize together relatively rapidly at ambient temperatures with no significant cross-hybridization. Unfortunately, to date such an assay system has been unavailable.

SUMMARY

The invention satisfies this need. The invention is an assay system, kit, and methods useful for sorting, detecting, and identifying analytes. The assay system comprises one or more pairs of complementary oligonucleotides where each oligonucleotide of a pair is at least partially complementary to the other oligonucleotide of the pair and the oligonucleotides have sequences designed to minimize cross-hybridization between different pairs. Preferably, the different oligonucleotide pairs hybridize at substantially the same rate, have substantially the same Tm, and hybridize together relatively rapidly at ambient temperatures without detectable cross-hybridization. Each oligonucleotide pair comprises a first oligonucleotide and a second oligonucleotide. An analyte binding agent is attached to the first oligonucleotide of a pair. The second oligonucleotide of a pair is immobilized to a solid support. In preferred embodiments, the oligonucleotides are selected from the group consisting of sequences having 12 or more consecutive nucleotides from SEQ ID NOS: 1–188. The invention further includes a method of generating nucleic acid sequences for complementary oligonucleotide pairs for use in the assay system, kit, and methods.

DRAWING

These features, aspects and advantages of the present invention will become better understood with regard to the following description, appended claims and accompanying figure where:

FIG. 1 illustrates a sandwich assay scheme having features of the invention.

SEQUENCE LISTING

Accompanying this application is a single diskette that contains the nucleotide sequences referenced to herein; and the information on the diskette is incorporated herein by reference.

DESCRIPTION

The following discussion describes embodiments of the invention and several variations of these embodiments. This discussion should not be construed, however, as limiting the invention to those particular embodiments. Practitioners skilled in the art will recognize numerous other embodiments as well. In all of the embodiments described herein that are referred to as being preferred or particularly preferred, these embodiments are not essential even though they may be preferred.

Definitions

The terms "nucleic acid" and "polynucleotide" are used herein interchangeably to include naturally occurring or synthesized double stranded deoxyribonucleic acid (hereinafter "DNA"), single stranded DNA, or ribonucleic acid (hereinafter "RNA").

The term "oligonucleotide" as used herein is a nucleic acid that includes linear oligomers of natural or modified monomers, a modified backbone, or modified linkages, including deoxyribonucleosides, ribonucleosides, anomeric forms thereof, peptide nucleic acids (PNAs), and the like, capable of specifically binding to an oligonucleotide or a polynucleotide target by way of a regular pattern of monomer-to-monomer interactions, such as Watson-Crick type of base pairing, or the like. Usually monomers are linked by phosphodiester bonds or analogs thereof to form oligonucleotides ranging in size from a few monomeric units, e.g. 3–4, to several tens of monomeric units. Analogs of phosphodiester linkages include phosphorothioate, phosphorodithioate, phosphoranilidate, phosphoramidate, and the like. Alternative chemistries, such as phosphorothioate, phosphoramidate, and similar such groups resulting in a non-natural backbone may also be used provided that the hybridization efficiencies of the resulting oligonucleotides is not adversely affected. The oligonucleotides can be synthesized by a number of approaches, e.g. Ozaki et al, Nucleic Acids Research, 20:5205–5214 (1992); Agrawal et al, Nucleic Acids Research, 18:5419–5423 (1990); or the like.

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind and form a duplex, or complementarity may be "complete" such that total complementarity exists between the single stranded molecules. The degree of complementarity between the nucleic acid strands has significant effects on the efficiency and strength of the hybridization between the nucleic acid strands.

A nucleic acid "duplex" is formed by the base pairing of complementary strands of DNA or RNA that form antiparallel complexes in which the 3'-terminal end of one strand is oriented and bound to the 5'-terminal end of the opposing strand. This base pairing also comprehends the pairing of "nucleoside analogs", such as deoxyinosine, nucleosides with 2-aminopurine bases, and the like, that may be employed. As used herein, "nucleoside" includes the natural nucleosides, including 2'-deoxy and 2'-hydroxyl forms, e.g. as described in Kornberg and Baker, *DNA Replication, 2nd Ed.* (Freeman, San Francisco, 1992). "Analogs" in reference to nucleosides includes synthetic nucleosides having modified base moieties and/or modified sugar moieties that are capable of specific hybridization, e.g. described by Scheit, *Nucleotide Analogs* (John Wiley, N.Y., 1980); Uhlman and Peyman, *Chemical Reviews*, 90:543–584 (1990), or the like. Such analogs include synthetic nucleosides designed to enhance binding properties, reduce degeneracy, increase specificity, and the like.

The terms "hybridize" or "hybridization" are intended to include admixing of at least two nucleic acid sequences under conditions such that when at least two complementary nucleic acid sequences are present, they will form a double-stranded structure through base-pairing.

The invention is directed to an assay system for an analyte. The assay system comprises one or more pair of complementary oligonucleotides. Each pair of complementary oligonucleotides comprises a first oligonucleotide and a second oligonucleotide. An analyte binding agent is attached to the first oligonucleotide of an oligonucleotide pair. In a preferred embodiment, there are different analyte binding agents linked to the first oligonucleotide of each pair and each different analyte binding agent having a specificity for a different analyte in one or more sample. The second oligonucleotide of an oligonucleotide pair is immobilized to a solid support.

The oligonucleotides of the invention are selected to have sequences that minimize the cross-hybridization of oligonucleotides from different oligonucleotide pairs. Each pair of complementary oligonucleotides typically comprises the same total number of nucleotides or a total number of nucleotides that differs by less than two to five oligonucleotides, and more typically differing by three oligonucleotides or less. The guanine and cytosine content, in combination, "GC content" of each oligonucleotide is typically between about 35% and about 65%, and more typically the GC content of each oligonucleotide is between about 50% and about 60%. Preferably, each pair of complementary oligonucleotides has substantially the same Tm (melting temperature) under preselected hybridization conditions. The oligonucleotides of the invention include SEQ ID NO: 1-SEQ ID NO: 188, and variations and subportions thereof, where SEQ ID NO: 1 is complementary to SEQ ID NO: 2, SEQ ID NO: 3 is complementary to SEQ ID NO: 4, SEQ ID NO: 5 is complementary to SEQ ID NO: 6, and so on. The oligonucleotides represented by SEQ ID NOS: 1–188 are shown in Table I.

Oligonucleotides comprising subportions of the above sequences are typically selected from the group consisting of the following: sequences having 12 or more consecutive nucleotides from SEQ ID NOS: 1–188; sequences having 14 or more consecutive nucleotides from SEQ ID NOS: 1–188; sequences having 16 or more consecutive nucleotides from SEQ ID NOS: 1–188; sequences having 18 or more consecutive nucleotides from SEQ ID NOS: 1–188; sequences having 20 or more consecutive nucleotides from SEQ ID NOS: 1–188; sequences having 22 or more consecutive nucleotides from SEQ ID NOS: 1–188; sequences having 24 or more consecutive nucleotides from SEQ ID NOS: 1–188; sequences having 26 or more consecutive nucleotides from SEQ ID NOS: 1–188; sequences having 28 or more consecutive nucleotides from SEQ ID NOS: 1–188; or sequences according to SEQ ID NOS: 1–188. Consecutive nucleotides are those which are typically linked directly together by phosphodiester bonds in a polynucleotide chain or strand. Alternatively, oligonucleotides are selected from the group consisting of sequences having one nucleotide variation in any nucleotide of sequences according to SEQ ID NOS: 1–188; oligonucleotides having two or fewer nucleotide variations in any two or fewer nucleotides of sequences according to SEQ ID NOS: 1–188; oligonucleotides having three or fewer nucleotide variations in any three or fewer nucleotides of sequences according to SEQ ID NOS: 1–188; oligonucleotides having four or fewer nucleotide variations in any four or fewer nucleotides of sequences according to SEQ ID NOS: 1–188; and oligonucleotides having five or fewer nucleotide variations in any five or fewer nucleotides of sequences according to SEQ ID NOS: 1–188. The assay system alternatively uses one or more oligonucleotide pair according to SEQ ID NO: 1–188 or variants thereof described herein; ten oligonucleotide pair according to SEQ ID NO: 1–188 or variants thereof described herein, ten or more oligonucleotide pair according to SEQ ID NO: 1–188 or variants thereof described herein, fourteen or more oligonucleotide pair according to SEQ ID NO: 1–188 or variants thereof described herein, and all oligonucleotide pairs according to SEQ ID NO: 1–188 or variants thereof described herein.

In particular embodiments the invention is an assay system for an analyte comprising ten and fourteen pair of complementary oligonucleotides. Each pair of complementary oligonucleotides comprises a first oligonucleotide and a second oligonucleotide, wherein the first oligonucleotide has an analyte binding agent attached thereto and the second oligonucleotide is immobilized to a solid support. The oligonucleotides are selected from the group consisting of sequences having 12 or more consecutive nucleotides from the group consisting of SEQ ID NO: 11; SEQ ID NO: 57; SEQ ID NO: 59; SEQ ID NO.65; SEQ ID NO: 67; SEQ ID NO: 69; SEQ ID NO: 75; SEQ ID NO: 77; SEQ ID NO: 93; SEQ ID NO: 95; SEQ ID NO: 117; SEQ ID NO: 123; SEQ ID NO: 129; SEQ ID NO: 163; and SEQ ID NO: 187 and the respective complementary oligonucleotides thereof represented as SEQ ID NO: 12; SEQ ID NO: 58; SEQ ID NO: 60; SEQ ID NO.66; SEQ ID NO: 68; SEQ ID NO: 70; SEQ ID NO: 76; SEQ ID NO: 78; SEQ ID NO: 94; SEQ ID NO: 96; SEQ ID NO: 118; SEQ ID NO: 124; SEQ ID NO: 130; SEQ ID NO: 164; and SEQ ID NO: 188.

In some embodiments, the oligonucleotides further comprise one or more linker molecule or linker nucleic acid sequence covalently linked to the oligonucleotides having sequences according to SEQ ID NOS: 1–188, or subportions thereof. The linker molecules or linker nucleic acid sequences are typically at the 5'-end or the 3'-end of the oligonucleotides, thus extending beyond the region of the oligonucleotide that is base-paired with the other oligonucleotide of the pair. The linker molecule or linker nucleic acid sequence, when present, typically links and attaches a first oligonucleotide of a pair to an analyte binding agent or links a second oligonucleotide of a pair to a solid support. Techniques for attaching oligonucleotides to various solid supports are well known in the art, such as described in Matson, R., et al; Biopolymer Synthesis on Polypropylene Supports: Oligonucleotide Arrays; Analytical Biochemistry 224, 110–116 (1995); Milton, R., U.S. Pat. No. 6,146,833; Hermanson, et al., "Immobilized Affinity Ligand Techniques," pages 64–67 (1992 Academic Press Inc.), the contents of which are incorporated by reference in their entirety. Techniques for attaching oligonucleotides to proteins and antibodies are well known in the art, such as described in Reddy et al., U.S. Pat. No. 5,648,213.

Hybridization reaction conditions are preferably preselected such that each oligonucleotide hybridizes only to its complementary paired oligonucleotide in a mixture of oligonucleotides from the assay system. As referred to herein, hybridizing only to its complementary paired oligonucleotide means no cross-hybridization greater than 0.1%, and preferably no cross-hybridization greater than 0.01%. It is further preferable that under mild reaction conditions oligonucleotides from different pairs exhibit no cross-hybridization greater than 0.1%, and preferably no cross-hybridization greater than 0.01%. For example, such mild conditions would include incubation for 1 hour at ambient room temperature in a reaction mixture comprising 50–150 mM NaCl in Tris-buffered saline. Under these conditions, the oligonucleotide pairs of the invention hybridize together with no cross-hybridization greater than 0.1%, and preferably no cross-hybridization greater than 0.01%. Ambient room temperature is generally understood to include a broad range of interior room temperatures naturally occurring or with climate control which generally fall into the range of from about 50 degrees F. to about 100 degrees F., more typically from about 65 degrees F. to about 85 degrees F., and most typically between about 68 degrees F. to about 80 degrees F.

Cross-hybridization between oligonucleotide pairs is in part minimized by selecting nucleotide sequences where oligonucleotides from different pairs have a very low degree of complementarity. Further, it is preferable that oligonucleotides from different pairs have a very low amount of complementarity when the alignment of one of the oligonucleotides is shifted relative to the other, including the introduction of a gap or the formation of a loop containing at least some nucleotides that do not undergo base-pairing with the paired oligonucleotide.

Cross-hybridization is tested in an assay system using a set of second oligonucleotides according to SEQ ID NOS: 1–188, and a single first oligonucleotide attached to an analyte binding agent. An assay is performed using a relatively high concentration of the single analyte (a concentration near the maximum measurable amount for that assay system), and cross-hybridization is detected as a signal from any other second oligonucleotide position in the assay. Cross-hybridization is quantified by estimating the amount of analyte corresponding to the cross-hybridizing signal (determined from a calibration curve of analyte assayed in parallel), expressed as a percentage of the amount of analyte in the sample. For example, an assay of a sample containing 10,000 pg/ml of a single analyte that gives a false-positive signal corresponding to 1 pg/ml of that analyte at a different oligonucleotide position (due to cross-hybridization of the first oligonucleotide to a non-complementary second oligonucleotide) would represent a cross-hybridization of 0.01% (1 pg/ml divided by 10,000 pg/ml×100%).

Further provided is an array comprising second oligonucleotides, and complementary first oligonucleotides attached to analyte binding molecules, such that an array of analyte binding molecules 'self-assemble' upon hybridization of the first and second oligonucleotides under preselected hybridization conditions. The term 'self-assemble' means that the hybridization localizes specific oligonucleotide-tagged binding molecules to specific positions in an array, forming or assembling an array of binding molecules from solution.

The invention further includes a method of generating nucleic acid sequences for complementary oligonucleotide pairs suitable for use in the assay system. The method comprises the steps of a) selecting one or more first sequences with pre-selected length and GC content such as a sequence shown in U.S. Pat. No. 5,648,213, and preferably at least a 35% GC content; b) generating a library of random sequences with about the same length, and preferably substantially the same length, and about the same GC content, and preferably substantially the same GC content, as the first one or more sequence; c) selecting a second sequence from the library of random sequences; d) discarding second oligonucleotide sequences, where the selection of the second to be discarded is made by comparing the second sequence with the first sequence, wherein the second sequence is rejected and discarded if either i) there are greater than 5 matches in any window of 8 bases in any alignment of the two sequences, or ii) the second sequence contains greater than 4 consecutive bases that are the same; e) adding those second sequences not discarded to the first sequences; and f) optionally, repeating steps c), d), and e) to form a collection of sequences. The method optionally further comprises the step of using a computer algorithm, such as NetPrimer 2.0 available from Premier Biosoft International, 3786 Corina Way, Palo Alto, Calif. 94303-4504 to analyze each retained sequence for potential secondary structure or self-complementarity, wherein sequences with significant predicted secondary structure or self-complementarity structure are rejected. The retained sequences are typically tested for cross-hybridization under relatively mild reaction conditions, for example under physiological salt conditions at ambient temperature, using a sensitive binding assay that can discriminate between hybridization of complementary and non-complementary pairs and can detect cross-hybridization of 0.1% or lower. Sequences are rejected that show greater than 0.1% cross-hybridization with any other sequence in the retained set. Two sequences have about the same length if the length differs by 5 or less nucleotides. Two sequences are considered to have substantially the same length if the length differs by 1 or 0 nucleotides. Two sequences have about the same GC content if the difference in GC content is no more than 30% different, and have substantially the same GC content if the difference is no more than 10% different.

The analyte binding agent typically comprises a protein or polypeptide that is capable of specifically binding with an analyte of interest. Preferably, the analyte binding agent is a monoclonal or polyclonal antibody to the analyte, or antigen-binding fragments thereof (e.g., Fab', $F(ab')_2$). Antibodies or antigen-binding fragments thereof is further understood to include chimeric, humanized, recombinant, and other such forms of antibodies. The analyte binding agent encompasses analogues and variants of various immunoreactants (for example, those generated using recombinant DNA techniques) which specifically bind to the target analyte. Also contemplated as within the scope of the invention are the formation of specific binding pairs comparable to the binding of an antibody to an antigen that can be implemented through the use of other specific protein-based, peptide-based, nucleic acid-based, carbohydrate-based, or lipid-based binding systems, such as for example a receptor protein or fragment thereof and an analyte ligand, polynucleotide and polynucleotide binding pairs, polynucleotide and protein binding pairs, lipid and protein binding pairs, enzyme and enzyme binding pairs, enzyme and substrate binding pairs, enzyme and inhibitor binding pairs, enzyme and metabolite binding pairs, carbohydrate and protein binding pairs, carbohydrate and lectin binding pairs, protein and drug binding pairs, and the like. Further contemplated as within the scope of the invention are chemical-based molecular receptor systems that selectively bind an analyte of interest.

In the embodiment illustrated in FIG. 1, the assay system utilizes a sandwich assay. The analyte binding agent attached to the first oligonucleotide is a capture antibody specific for the analyte. For each pair of oligonucleotides, the first oligonucleotide hybridizes to the second oligonucleotide, which is directly attached to the solid substrate. The first oligonucleotide of the pair becomes immobilized to the solid substrate via its hybridization to the second oligonucleotide. The capture antibody is specific for a particular analyte, and this analyte becomes attached to a solid support via its binding to the capture antibody. The capture antibodies are typically specific for different analytes, and the spacial position of the capture antibodies on the solid substrate is determined by the location of the second oligonucleotide of each pair on the solid substrate. The analytes are detected via a secondary antibody, termed a detection antibody, which has a detection moiety attached thereto. In the embodiment illustrated in FIG. 1, the detection moiety is the fluorescent label PBXL-1 (available from Martek, 6480 Dobbin Road, Columbia, Md. 21045). Fluorophores and fluorescent dyes that can be used as detection moieties are well known in the art. Other suitable detection moieties include, for example, substrates for enzymatic-based detection, radioactive labels, and the like. Alternative methods of detection of analytes bound are envisioned to be within the scope of the invention, such as for example competitive assays and primer extension assays.

In some embodiments, the solid support comprises a planar surface in which each of the different oligonucleotides is attached to a different predefined region of the substantially planar surface. The solid support typically comprises microarray substrates including but not limited to: flat microscope slides; flexible membranes made of nitrocellulose, nylon, and PVDF; and microwell plates made of glass, polystyrene, polypropylene, and polycarbonate.

In alternative embodiments, the solid support is a bead, particle, micro particle, or the like, and the terms bead, particle, and micro particle are used interchangeably herein. The beads typically have diameters in the range of from about 0.04 to about 50 micrometers. In one embodiment of the present invention, the beads are in a size range from about 0.1 to about 20 micrometers. The beads are typically suspended in a liquid such that their density is within the range of between about 0.5 to about 2.0 grams per milliliter. The size and density of bead suspension allow beads to be treated as simple liquids by most fluid transfer apparatus such as pipettes, pumps, and certain valves. The materials and methods that are used to prepare the beads are well known in the art.

Typically, the analyte detected by the assay system is selected from the group consisting of polypeptides or proteins, carbohydrates, ligands, nucleic acids, lipids, including but not limited to antibodies and binding fragments thereof, hormones, lectins, receptors, steroids, cell-surface antigens, cytokines, viral antigens, bacterial antigens, cDNA, and drugs of abuse. In a preferred embodiment, the assay system is provided in the form of a kit for the detection of one or more specific analyte.

TABLE I

| | |
|---|---|
| SEQ ID NO 1: | 5'-ATACTGACTGGCGATGCTGTCGAAGTAGCG-3' |
| SEQ ID NO 2: | 5'-CGCTACTTCGACAGCATCGCCAGTCAGTAT-3' |
| SEQ ID NO 3: | 5'-AGTTAAATAGCTTGCAAAATACGTGGCCTT-3' |
| SEQ ID NO 4: | 5'-AAGGCCACGTATTTTGCAAGCTATTTAACT-3' |
| SEQ ID NO 5: | 5'-GAAGCCATACCAAACGACGAGCGTGACACC-3' |
| SEQ ID NO 6: | 5'-GGTGTCACGCTCGTCGTTTGGTATGGCTTC-3' |
| SEQ ID NO 7: | 5'-GCTTACCGAATACGGCTTGGAGAACCTATC-3' |
| SEQ ID NO 8: | 5'-GATAGGTTCTCCAAGCCGTATTCGGTAAGC-3' |
| SEQ ID NO 9: | 5'-GCGTGGTCCGCGATCTTCCTACGATTGATG-3' |
| SEQ ID NO 10: | 5'-CATCAATCGTAGGAAGATCGCGGACCACGC-3' |
| SEQ ID NO 11: | 5'-TTTGAGGTTTCGGAGCGTTCCGTGCATCGC-3' |
| SEQ ID NO 12: | 5'-GCGATGCACGGAACGCTCCGAAACCTCAAA-3' |
| SEQ ID NO 13: | 5'-AATCCTGTTGTGAGCCGACCAAGTGCCTCC-3' |
| SEQ ID NO 14: | 5'-GGAGGCACTTGGTCGGCTCACAACAGGATT-3' |
| SEQ ID NO 15: | 5'-GTATCTGACGCGTATGCCCAGGTTAGTGGC-3' |
| SEQ ID NO 16: | 5'-GCCACTAACCTGGGCATACGCGTCAGATAC-3' |
| SEQ ID NO 17: | 5'-CGGAGTCGTCCTCTGTAGGGATTTGCCCTT-3' |
| SEQ ID NO 18: | 5'-AAGGGCAAATCCCTACAGAGGACGACTCCG-3' |
| SEQ ID NO 19: | 5'-CAGGCTGTGGAGTGCTATTGTCATATGGGC-3' |
| SEQ ID NO 20: | 5'-GCCCATATGACAATAGCACTCCACAGCCTG-3' |
| SEQ ID NO 21: | 5'-TCTTCTCTCTGGTCTAAGGCATCGAGCGGA-3' |
| SEQ ID NO 22: | 5'-TCCGCTCGATGCCTTAGACCAGAGAGAAGA-3' |
| SEQ ID NO 23: | 5'-TGGCGTACTAGTGCTTAGGCGTACTGAAGC-3' |
| SEQ ID NO 24: | 5'-GCTTCAGTACGCCTAAGCACTAGTACGCCA-3' |
| SEQ ID NO 25: | 5'-TGCTGGCTTTACTGCGACGGTGACTCTCCT-3' |
| SEQ ID NO 26: | 5'-AGGAGAGTCACCGTCGCAGTAAAGCCAGCA-3' |
| SEQ ID NO 27: | 5'-CTATCAAAGCTGGTTCCAGGCGCTCCTGGA-3' |
| SEQ ID NO 28: | 5'-TCCAGGAGCGCCTGGAACCAGCTTTGATAG-3' |
| SEQ ID NO 29: | 5'-TGAGGCAAGTACATTAGTTCTCAGCCGGCG-3' |
| SEQ ID NO 30: | 5'-CGCCGGCTGAGAACTAATGTACTTGCCTCA-3' |
| SEQ ID NO 31: | 5'-GCTTGGGTTAGATTGTGTTTGCCGAGCCAA-3' |
| SEQ ID NO 32: | 5'-TTGGCTCGGCAAACACAATCTAACCCAAGC-3' |
| SEQ ID NO 33: | 5'-CGTCCATTCCTATCGGGAGGTAACAGACTT-3' |
| SEQ ID NO 34: | 5'-AAGTCTGTTACCTCCCGATAGGAATGGACG-3' |
| SEQ ID NO 35: | 5'-CTAAGGAGTCCGAAGATGTACAATGGGTCG-3' |
| SEQ ID NO 36: | 5'-CGACCCATTGTACATCTTCGGACTCCTTAG-3' |
| SEQ ID NO 37: | 5'-AACTAGCCGCCTCCTGTCCCATGAATTCTA-3' |

TABLE I-continued

SEQ ID NO 38:  5'-TAGAATTCATGGGACAGGAGGCGGCTAGTT-3'
SEQ ID NO 39:  5'-AGCTTCTTGTAACGTTGAGTTGCAGGTCCG-3'
SEQ ID NO 40:  5'-CGGACCTGCAACTCAACGTTACAAGAAGCT-3'
SEQ ID NO 41:  5'-CACTGGATAATTGCGCCTTCCGTGCATGAA-3'
SEQ ID NO 42:  5'-TTCATGCACGGAAGGCGCAATTATCCAGTG-3'
SEQ ID NO 43:  5'-CCCGCGCAGAGCGTAGTTGTAATTTAGATC-3'
SEQ ID NO 44:  5'-GATCTAAATTACAACTACGCTCTGCGCGGG-3'
SEQ ID NO 45:  5'-CCTGGAAATAAGCAGCAGCACCAACTCTCA-3'
SEQ ID NO 46:  5'-TGAGAGTTGGTGCTGCTGCTTATTTCCAGG-3'
SEQ ID NO 47:  5'-GGCTCATGGTTCTTTGCTCAACCATAAGCC-3'
SEQ ID NO 48:  5'-GGCTTATGGTTGAGCAAAGAACCATGAGCC-3'
SEQ ID NO 49:  5'-CTTGCTCCTCACATGATGCGGAAACGCTAA-3'
SEQ ID NO 50:  5'-TTAGCGTTTCCGCATCATGTGAGGAGCAAG-3'
SEQ ID NO 51:  5'-ATCCTTCTGCACTTTCGCGTAGACATAGCC-3'
SEQ ID NO 52:  5'-GGCTATGTCTACGCGAAAGTGCAGAAGGAT-3'
SEQ ID NO 53:  5'-ATCGAACCCAAACTGAGGTTAAGAGCCGCT-3'
SEQ ID NO 54:  5'-AGCGGCTCTTAACCTCAGTTTGGGTTCGAT-3'
SEQ ID NO 55:  5'-AAGGACTGGACGTTGCATTCACAGTGGGTT-3'
SEQ ID NO 56:  5'-AACCCACTGTGAATGCAACGTCCAGTCCTT-3'
SEQ ID NO 57:  5'-CTCATGAAGGCCGTCGGGAAATTCCAAGTT-3'
SEQ ID NO 58:  5'-AACTTGGAATTTCCCGACGGCCTTCATGAG-3'
SEQ ID NO 59:  5'-TGGATTCCGTTATCACCATTTGGACCCTGC-3'
SEQ ID NO 60:  5'-GCAGGGTCCAAATGGTGATAACGGAATCCA-3'
SEQ ID NO 61:  5'-TAAGGGCTCTATCTACCACCTCCGACTTTC-3'
SEQ ID NO 62:  5'-GAAAGTCGGAGGTGGTAGATAGAGCCCTTA-3'
SEQ ID NO 63:  5'-TACGCTCCCAGTGTGATCACCAAAGCTTAC-3'
SEQ ID NO 64:  5'-GTAAGCTTTGGTGATCACACTGGGAGCGTA-3'
SEQ ID NO 65:  5'-AGACTGAACTACCGGCGGTTGCACTACTAA-3'
SEQ ID NO 66:  5'-TTAGTAGTGCAACCGCCGGTAGTTCAGTCT-3'
SEQ ID NO 67:  5'-GCCAAACACGCCCAATCACTGTTACATGTC-3'
SEQ ID NO 68:  5'-GACATGTAACAGTGATTGGGCGTGTTTGGC-3'
SEQ ID NO 69:  5'-GCTTGACGTCTACCACCGTGAACATAAGGA-3'
SEQ ID NO 70:  5'-TCCTTATGTTCACGGTGGTAGACGTCAAGC-3'
SEQ ID NO 71:  5'-AAGAACCGTAATAGGCCCGGTTGGGAATTC-3'
SEQ ID NO 72:  5'-GAATTCCCAACCGGGCCTATTACGGTTCTT-3'
SEQ ID NO 73:  5'-CGGACTAACAAGACTCTTATAGCGTCTCGC-3'
SEQ ID NO 74:  5'-GCGAGACGCTATAAGAGTCTTGTTAGTCCG-3'
SEQ ID NO 75:  5'-TCGCCAACGTAGCTGTGCTACAGTTGATTC-3'
SEQ ID NO 76:  5'-GAATCAACTGTAGCACAGCTACGTTGGCGA-3'
SEQ ID NO 77:  5'-GCAGCGGCTAAACCTTGAGATCGAATGGAA-3'

TABLE I-continued

SEQ ID NO 78:  5'-TTCCATTCGATCTCAAGGTTTAGCCGCTGC-3'
SEQ ID NO 79:  5'-GCAACCGTCAACGGTCTTAATGACACATCG-3'
SEQ ID NO 80:  5'-CGATGTGTCATTAAGACCGTTGACGGTTGC-3'
SEQ ID NO 81:  5'-GGGTAGAAACGGACGTTACCCATGATCTTG-3'
SEQ ID NO 82:  5'-CAAGATCATGGGTAACGTCCGTTTCTACCC-3'
SEQ ID NO 83:  5'-GGCGGCAACACCTACCTTCTAGATTGAAAC-3'
SEQ ID NO 84:  5'-GTTTCAATCTAGAAGGTAGGTGTTGCCGCC-3'
SEQ ID NO 85:  5'-CGCTAATAGTGGACCCTCTCATAGCTATGG-3'
SEQ ID NO 86:  5'-CCATAGCTATGAGAGGGTCCACTATTAGCG-3'
SEQ ID NO 87:  5'-CTGATGGAATCTACCACTGCTAAACGCAGC-3'
SEQ ID NO 88:  5'-GCTGCGTTTAGCAGTGGTAGATTCCATCAG-3'
SEQ ID NO 89:  5'-GCCTAGTCGGATGCTCGGATATCATACTAC-3'
SEQ ID NO 90:  5'-GTAGTATGATATCCGAGCATCCGACTAGGC-3'
SEQ ID NO 91:  5'-CTTTGAACGACATCTTAGTCTCGAACGCCG-3'
SEQ ID NO 92:  5'-CGGCGTTCGAGACTAAGATGTCGTTCAAAG-3'
SEQ ID NO 93:  5'-TCGACATGCGCGTCATCTGATACTGCGGTC-3'
SEQ ID NO 94:  5'-GACCGCAGTATCAGATGACGCGCATGTCGA-3'
SEQ ID NO 95:  5'-GGTGGCCTCGTAAGGCGAGAATTAGGGTTG-3'
SEQ ID NO 96:  5'-CAACCCTAATTCTCGCCTTACGAGGCCACC-3'
SEQ ID NO 97:  5'-GGCTAGATAGGCGATTAGTCAGAGTGGACA-3'
SEQ ID NO 98:  5'-TGTCCACTCTGACTAATCGCCTATCTAGCC-3'
SEQ ID NO 99:  5'-CCTGGATAAGACGTTAACGTTACGGAGCCA-3'
SEQ ID NO 100: 5'-TGGCTCCGTAACGTTAACGTCTTATCCAGG-3'
SEQ ID NO 101: 5'-CAAACTGAGCTAGGCCTAACTGTGATGCAG-3'
SEQ ID NO 102: 5'-CTGCATCACAGTTAGGCCTAGCTCAGTTTG-3'
SEQ ID NO 103: 5'-CGCCTCGTGTGTTATAACGATGGGACTTTG-3'
SEQ ID NO 104: 5'-CAAAGTCCCATCGTTATAACACACGAGGCG-3'
SEQ ID NO 105: 5'-TGGTTTAGCCTTTCCGGCATCTGCTGTACA-3'
SEQ ID NO 106: 5'-TGTACAGCAGATGCCGGAAAGGCTAAACCA-3'
SEQ ID NO 107: 5'-CAACCTCTACCCAGAAACTCAAGTTTCGGC-3'
SEQ ID NO 108: 5'-GCCGAAACTTGAGTTTCTGGGTAGAGGTTG-3'
SEQ ID NO 109: 5'-CTCGTTTCTAGGTCACTGCGCAAAACGCTT-3'
SEQ ID NO 110: 5'-AAGCGTTTTGCGCAGTGACCTAGAAACGAG-3'
SEQ ID NO 111: 5'-TGCTCTTCTCGTGCCCGTTAAAGGATCGAT-3'
SEQ ID NO 112: 5'-ATCGATCCTTTAACGGGCACGAGAAGAGCA-3'
SEQ ID NO 113: 5'-CCCGGCAGGTATACAAAGCACTTCGTATAC-3'
SEQ ID NO 114: 5'-GTATACGAAGTGCTTTGTATACCTGCCGGG-3'
SEQ ID NO 115: 5'-GTAGAAGCCTGTGGTTAAAACTATGGCCCG-3'
SEQ ID NO 116: 5'-CGGGCCATAGTTTTAACCACAGGCTTCTAC-3'

TABLE I-continued

SEQ ID NO 117: 5'-CATCGGTCGAACCCGTGTCAACAAGATTCT-3'
SEQ ID NO 118: 5'-AGAATCTTGTTGACACGGGTTCGACCGATG-3'
SEQ ID NO 119: 5'-TGGAGGAGACTTGTCAGGATTTGCTCTGAG-3'
SEQ ID NO 120: 5'-CTCAGAGCAAATCCTGACAAGTCTCCTCCA-3'
SEQ ID NO 121: 5'-AGCCCAAGGAATAGTCAATACTTCCTCAGC-3'
SEQ ID NO 122: 5'-GCTGAGGAAGTATTGACTATTCCTTGGGCT-3'
SEQ ID NO 123: 5'-CAAAGGAAATGTTCGAGCCGCCAGACTAGA-3'
SEQ ID NO 124: 5'-TCTAGTCTGGCGGCTCGAACATTTCCTTTG-3'
SEQ ID NO 125: 5'-TCCTATTATGCCTGAATTCAGGCAGCCGAC-3'
SEQ ID NO 126: 5'-GTCGGCTGCCTGAATTCAGGCATAATAGGA-3'
SEQ ID NO 127: 5'-GCATGTGTAGATGGCCAGCCACTTATTAGG-3'
SEQ ID NO 128: 5'-CCTAATAAGTGGCTGGCCATCTACACATGC-3'
SEQ ID NO 129: 5'-CCTTTGGGTATTGCTCTGACCTGGTTATGC-3'
SEQ ID NO 130: 5'-GCATAACCAGGTCAGAGCAATACCCAAAGG-3'
SEQ ID NO 131: 5'-AGGCAGGTCCCTAGTCACAACTTAATCTGC-3'
SEQ ID NO 132: 5'-GCAGATTAAGTTGTGACTAGGGACCTGCCT-3'
SEQ ID NO 133: 5'-CCGACAGTACTTTACTCATTGTGGCGCAGT-3'
SEQ ID NO 134: 5'-ACTGCGCCACAATGAGTAAAGTACTGTCGG-3'
SEQ ID NO 135: 5'-AAGTGAAAGCATCTCCGCATGCATTGGCCA-3'
SEQ ID NO 136: 5'-TGGCCAATGCATGCGGAGATGCTTTCACTT-3'
SEQ ID NO 137: 5'-GCACGTACACGAGAAACGGGTATCTAAGCT-3'
SEQ ID NO 138: 5'-AGCTTAGATACCCGTTTCTCGTGTACGTGC-3'
SEQ ID NO 139: 5'-TCCAGCTGCAGACAAAGACCTATGCGTTAC-3'
SEQ ID NO 140: 5'-GTAACGCATAGGTCTTTGTCTGCAGCTGGA-3'
SEQ ID NO 141: 5'-ATCCGACTCATCTAGGTGCACCTCTATGTG-3'
SEQ ID NO 142: 5'-CACATAGAGGTGCACCTAGATGAGTCGGAT-3'
SEQ ID NO 143: 5'-CTGGACGACTTTCTAGATGCCCTGAGTTAC-3'
SEQ ID NO 144: 5'-GTAACTCAGGGCATCTAGAAAGTCGTCCAG-3'
SEQ ID NO 145: 5'-CTAAGACACATCCTATTATCCTGCCCGAGC-3'
SEQ ID NO 146: 5'-GCTCGGGCAGGATAATAGGATGTGTCTTAG-3'
SEQ ID NO 147: 5'-AGAATTGCGCACAAGAAGTCTCTGCGGCAA-3'
SEQ ID NO 148: 5'-TTGCCGCAGAGACTTCTTGTGCGCAATTCT-3'
SEQ ID NO 149: 5'-CCGAGCACTATAGGAGTTATAATCGAGGGG-3'
SEQ ID NO 150: 5'-CCCCTCGATTATAACTCCTATAGTGCTCGG-3'
SEQ ID NO 151: 5'-CTAGTTACCCACACTTAGTCACTTGCAGCG-3'
SEQ ID NO 152: 5'-CGCTGCAAGTGACTAAGTGTGGGTAACTAG-3'
SEQ ID NO 153: 5'-GCAAATCAGTAAAGATGGACAGGCCTACCC-3'
SEQ ID NO 154: 5'-GGGTAGGCCTGTCCATCTTTACTGATTTGC-3'
SEQ ID NO 155: 5'-ATGGTCGCATGATTTAGTACGGATGGCGTG-3'
SEQ ID NO 156: 5'-CACGCCATCCGTACTAAATCATGCGACCAT-3'

SEQ ID NO 157: 5'-AACATTCTTCTCGGGTTACAAACCGCGCGA-3'
SEQ ID NO 158: 5'-TCGCGCGGTTTGTAACCCGAGAAGAATGTT-3'
SEQ ID NO 159: 5'-GGCAAGACTCGTTCTGGGCTGCTTATTAGA-3'
SEQ ID NO 160: 5'-TCTAATAAGCAGCCCAGAACGAGTCTTGCC-3'
SEQ ID NO 161: 5'-CCATATCACGTGATGCCGGAATTGTCACGT-3'
SEQ ID NO 162: 5'-ACGTGACAATTCCGGCATCACGTGATATGG-3'
SEQ ID NO 163: 5'-TGCGATATACTCCATGCCTCTCTTGGCGGA-3'
SEQ ID NO 164: 5'-TCCGCCAAGAGAGGCATGGAGTATATCGCA-3'
SEQ ID NO 165: 5'-GTGTGCGCGCCTTCTAGAATACTCATAAGC-3'
SEQ ID NO 166: 5'-GCTTATGAGTATTCTAGAAGGCGCGCACAC-3'
SEQ ID NO 167: 5'-CCAGCACAAACGCTGATCGTTGAAACGGAT-3'
SEQ ID NO 168: 5'-ATCCGTTTCAACGATCAGCGTTTGTGCTGG-3'
SEQ ID NO 169: 5'-AAGTGTGAGGTCGTTCACTTTCACACTGCC-3'
SEQ ID NO 170: 5'-GGCAGTGTGAAAGTGAACGACCTCACACTT-3'
SEQ ID NO 171: 5'-TAAATCAACGGCATTGGCGTCCGTTATCGC-3'
SEQ ID NO 172: 5'-GCGATAACGGACGCCAATGCCGTTGATTTA-3'
SEQ ID NO 173: 5'-TGCGCCCACACGTTACGATCTGTATAAAGC-3'
SEQ ID NO 174: 5'-GCTTTATACAGATCGTAACGTGTGGGCGCA-3'
SEQ ID NO 175: 5'-ATAATGCGTTTCCGGCCACCGCGTTATTAC-3'
SEQ ID NO 176: 5'-GTAATAACGCGGTGGCCGGAAACGCATTAT-3'
SEQ ID NO 177: 5'-TCAACGCGCGGTTTCTTGAGTAATTCAGCC-3'
SEQ ID NO 178: 5'-GGCTGAATTACTCAAGAAACCGCGCGTTGA-3'
SEQ ID NO 179: 5'-GCACCGGAGGTTTACATCATGCAGAAGTGT-3'
SEQ ID NO 180: 5'-ACACTTCTGCATGATGTAAACCTCCGGTGC-3'
SEQ ID NO 181: 5'-TGTCTCACTAGAGCTTCACCCATGCATGTG-3'
SEQ ID NO 182: 5'-CACATGCATGGGTGAAGCTCTAGTGAGACA-3'
SEQ ID NO 183: 5'-GCCAAACATAGTTGGAATCCTCGGGAGGAA-3'
SEQ ID NO 184: 5'-TTCCTCCCGAGGATTCCAACTATGTTTGGC-3'
SEQ ID NO 185: 5'-GCACTATAAACTTCCTAGCCTTCTCGTCGC-3'
SEQ ID NO 186: 5'-GCGACGAGAAGGCTAGGAAGTTTATAGTGC-3'
SEQ ID NO 187: 5'-GGTTTGCAAGAAGCAGAAGCCATTCCGACA-3'
SEQ ID NO 188: 5'-TGTCGGAATGGCTTCTGCTTCTTGCAAACC-3'

Having thus described the invention, it should be apparent that numerous modifications and adaptations may be resorted to without departing from the scope and fair meaning of the instant invention as set forth hereinabove and as described hereinbelow by the claims.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

What is claimed is:

1. An assay system for an analyte comprising:
a) a solid support; and
b) ten or more pairs of oligonucleotides, each oligonucleotide of the pair is at least partially complementary to the other oligonucleotide of the pair, each pair comprises a first oligonucleotide and a second oligonucleotide, the first oligonucleotide comprising an analyte binding agent attached thereto, the second oligonucleotide being immobilized to the solid support, wherein the first and second oligonucleotides comprise 16 or more consecutive nucleotides from the set of oligonucleotides selected from the group consisting of SEQ ID NOS: 1–188 wherein at least one of the oligonucleotides comprises 16 or more consecutive nucleotides from the group consisting of SEQ ID NOS: 11, 57, 59, 65, 67, 69, 75, 77, 93, 117, 123, 129, 163, and 187.

2. The assay system of claim 1, wherein the first and second oligonucleotides comprise 20 or more consecutive nucleotides from the set of oligonucleotides selected from the group consisting of SEQ ID NOS: 1–188.

3. The assay system of claim 1, wherein the first and second oligonucleotides comprise 24 or more consecutive nucleotides from the set of oligonucleotides selected from the group consisting of SEQ ID NOS: 1–188.

4. The assay system of claim 1, wherein the first and second oligonucleotides comprise 28 or more consecutive nucleotides from the set of oligonucleotides selected from the group consisting of SEQ ID NOS: 1–188.

5. The assay system of claim 1, wherein the ten or more pairs of oligonucleotides are selected from the group consisting of sequences according to SEQ ID NOS: 1–188.

6. The assay system of claim 1, wherein there are 12 or more pairs of oligonucleotides having 16 or more consecutive nucleotides from the set of oligonucleotides selected from the group consisting of SEQ ID NOS: 1–188.

7. The assay system of claim 1, wherein there are 14 or more pairs of oligonucleotides having 16 or more consecutive nucleotides from the set of oligonucleotides selected from the group consisting of SEQ ID NOS: 1–188.

8. The assay system of claim 1, wherein there are 15 pairs of oligonucleotides having 16 or more consecutive nucleotides from the set of oligonucleotides selected from the group consisting of SEQ ID NOS: 1–188.

9. The assay system of claim 1, wherein the oligonucleotides are selected from the group consisting of sequences according to SEQ ID NO: 11; SEQ ID NO: 57; SEQ ID NO: 59; SEQ ID NO.65; SEQ ID NO: 67; SEQ ID NO: 69; SEQ ID NO: 75; SEQ ID NO: 77; SEQ ID NO: 93; SEQ ID NO: 95; SEQ ID NO: 117; SEQ ID NO: 123; SEQ ID NO: 129; SEQ ID NO: 163; SEQ ID NO: 187, and complements of the preceding.

10. The assay system of claim 1, wherein there are different analyte binding agents linked to the first oligonucleotide of each pair, each different analyte binding agent having a specificity for a different analyte in one or more sample.

11. The assay system of claim 1, wherein one or both oligonucleotides from one or more oligonucleotide pairs further comprises a linker molecule or linker nucleic acid sequence attached thereto.

12. The assay system of claim 11, wherein the linker nucleic acid sequence is covalently bonded to the one oligonucleotide from one or more oligonucleotide pairs and the linker nucleic acid is covalently bonded to the solid support and the linker nucleic acid attaches the oligonucleotide to the solid support.

13. The assay system of claim 1, wherein the oligonucleotide pairs hybridize together at ambient temperature with no cross-hybridization greater than 0.1%.

14. The assay system of claim 1, wherein the analyte binding agent of the first oligonucleotide is selected from the group consisting of antibodies and antigen binding fragments thereof.

15. The assay system of claim 1, wherein each of the different oligonucleotides is attached to the surface of the solid support in a different predefined region.

16. The assay system of claim 1, wherein the solid support is a bead.

17. The assay system of claim 1, wherein the analyte is selected from the group consisting of polypeptides or proteins, carbohydrates, ligands, nucleic acids, lipids, steroids, metabolites, drugs of abuse, viral antigens, and bacterial antigens.

18. The assay system of claim 14, wherein the analyte is a protein or polypeptide selected from the group consisting of antibodies and binding fragments thereof, hormones, lectins, receptors, steroids, cell-surface antigens, cytokines, growth factors, disease markers, and oncogenic markers.

19. The assay system of claim 1 provided in the form of a kit for the detection of one or more specific analyte.

20. An assay system for an analyte comprising one or more pairs of complementary oligonucleotides, each pair of complementary oligonucleotides comprising a first oligonucleotide and a second oligonucleotide, the first oligonucleotide having an analyte attached thereto, the second oligonucleotide being immobilized to a solid support, the oligonucleotides are selected from the group consisting of sequences having 16 or more consecutive nucleotides from the group consisting of SEQ ID NO: 11; SEQ ID NO: 57; SEQ ID NO: 59; SEQ ID NO.65; SEQ ID NO: 67; SEQ ID NO: 69; SEQ ID NO: 75; SEQ ID NO: 77; SEQ ID NO: 93; SEQ ID NO: 117; SEQ ID NO: 123; SEQ ID NO: 129; SEQ ID NO: 163; SEQ ID NO: 187, and complements of the preceding.

21. An assay system for an analyte comprising at least ten pairs of complementary oligonucleotides, each pair of complementary oligonucleotides comprising a first oligonucleotide and a second oligonucleotide, the first oligonucleotide having an analyte attached thereto, the second oligonucleotide being immobilized to a solid support, the oligonucleotides are selected from the group consisting of sequences having 16 or more consecutive nucleotides from the group consisting of SEQ ID NO: 11; SEQ ID NO: 57; SEQ ID NO: 59; SEQ ID NO.65; SEQ ID NO: 67; SEQ ID NO: 69; SEQ ID NO: 75; SEQ ID NO: 77; SEQ ID NO: 93; SEQ ID NO: 117; SEQ ID NO: 123; SEQ ID NO: 129; SEQ ID NO: 163; SEQ ID NO: 187, and complements of the preceding.

22. A set of oligonucleotides having a nucleic acid sequence selected from the group consisting of sequences having 16 or more consecutive nucleotides from SEQ ID NOs: 1–188 wherein at least one of the oligonucleotides comprises 16 or more consecutive nucleotides from the group consisting of SEQ ID NOS: 11, 57, 59, 65, 67, 69, 75, 77, 93, 117, 123, 129, 163, and 187.

23. A set of one or more complementary oligonucleotide pairs having a nucleic acid sequence consisting of one or more oligonucleotides selected from the group consisting of sequences having 16 or more consecutive nucleotides from SEQ ID NOS: 1–188 wherein at least one of the oligonucleotides comprises 16 or more consecutive nucleotides from the group consisting of SEQ ID NOs: 11, 57, 59, 65, 67, 69, 75, 77, 93, 117, 123, 129, 163, and 187.

24. A method of detecting an analyte in a sample, the method comprising the steps of:
  a) selecting one or more complementary oligonucleotide pairs, each pair having a first oligonucleotide and a second oligonucleotide, the first oligonucleotide comprising an analyte binding agent attached thereto, the second oligonucleotide being immobilized to a solid support, the first or second oligonucleotide of a pair having a nucleic acid sequence selected from the group consisting of sequences having 16 or more consecutive nucleotides from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29; SEQ ID NO: 31; SEQ ID NO: 35; SEQ ID NO: 37; SEQ ID NO: 39; SEQ ID NO: 41; SEQ ID NO: 43; SEQ ID NO: 45; SEQ ID NO: 47; SEQ ID NO: 49; SEQ ID NO: 51; SEQ ID NO: 53; SEQ ID NO: 55; SEQ ID NO: 57; SEQ ID NO: 63; SEQ ID NO: 73; SEQ ID NO: 75; SEQ ID NO: 81; SEQ ID NO: 83; SEQ ID NO: 85; SEQ ID NO: 87; SEQ ID NO: 89; SEQ ID NO: 91; SEQ ID NO: 93; SEQ ID NO: 95; SEQ ID NO: 97; SEQ ID NO: 99; SEQ ID NO: 101; SEQ ID NO: 103; SEQ ID NO: 105; SEQ ID NO: 107; SEQ ID NO: 109; SEQ ID NO: 111; SEQ ID NO: 113; SEQ ID NO: 115; SEQ ID NO: 117; SEQ ID NO: 119; SEQ ID NO: 121; SEQ ID NO: 123; SEQ ID NO: 125; SEQ ID NO: 127; SEQ ID NO: 129; SEQ ID NO: 131; SEQ ID NO: 133; SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 185, SEQ ID NO: 187 wherein at least one of the first or second oligonucleotides of the pair is selected from the group consisting of sequences having 16 or more consecutive nucleotides from the group consisting of SEQ ID NOs; 11, 57, 75, 93, 117, 127, 129, 163, and 187" and a complementary oligonucleotide for each of the one or more of the preceding;
  b) providing a sample comprising one or more analyte;
  c) admixing one or more analytes with the first oligonucleotide under conditions where the analyte binding agents are able to bind to their respective analytes and admixing the one or more oligonucleotide pairs under conditions that facilitates the selective hybridization of complementary oligonucleotides to form hybridized oligonucleotides with bound analyte; and
  d) detecting one or more bound analytes.

* * * * *